United States Patent
Mann

[19]

[11] Patent Number: 5,860,896
[45] Date of Patent: Jan. 19, 1999

[54] POSTURE-AIDING DEVICE

[76] Inventor: Paula Mann, 230 E. 88th St., Apt. 12H, New York, N.Y. 10128

[21] Appl. No.: 998,676
[22] Filed: Dec. 29, 1997
[51] Int. Cl.$^6$ ..................................................... A63B 21/02
[52] U.S. Cl. ........................... 482/122; 482/124; 482/121
[58] Field of Search ................................... 482/121, 122, 482/124, 126

[56] References Cited

U.S. PATENT DOCUMENTS

| | | | |
|---|---|---|---|
| 2,224,103 | 12/1940 | Nilson | 482/121 |
| 4,852,874 | 8/1989 | Sleichter, III et al. | 482/122 |
| 5,230,682 | 7/1993 | Myers | 482/122 |
| 5,318,494 | 6/1994 | Santighian | 482/121 |
| 5,573,487 | 11/1996 | Wallner | 482/124 |

*Primary Examiner*—Lynne A. Reichard
*Attorney, Agent, or Firm*—Myron Amer PC

[57] ABSTRACT

A posture-aiding elastic band that is worn with the user's upper arms inserted through loops formed at opposite ends of the band and with the length portions against each other, the band is stretched across the back of the user, which back width typically does not significantly vary among individuals so that one-size-fits-all and wherein there is urgency induced in the band due to the stretching which urges the upper arms or shoulders in movement into a vertical plane of the user's back providing a favorable contribution to the user's appearance and causing the user to develop a habit against slouching his/her shoulders and assuming a less desirable posture.

1 Claim, 2 Drawing Sheets

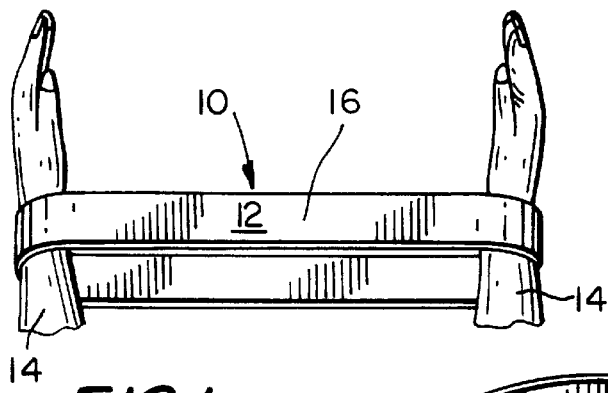
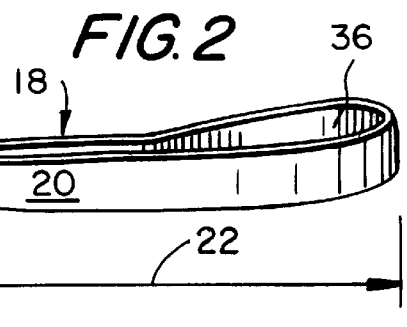
FIG. 1 PRIOR ART
FIG. 2
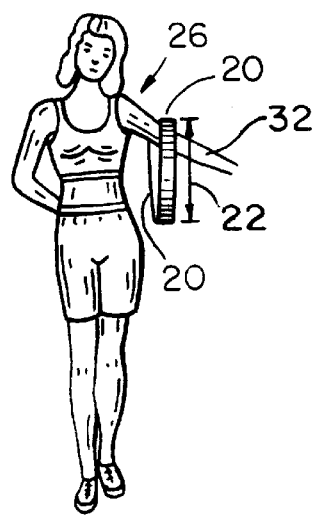
FIG. 3
FIG. 4
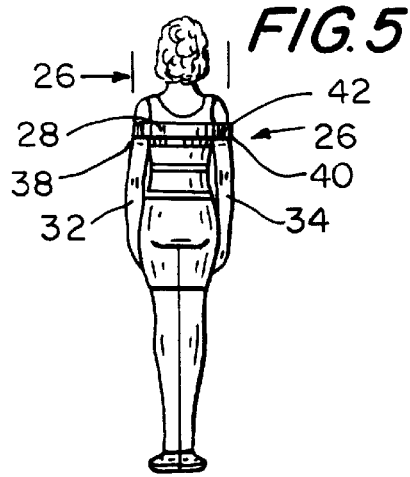
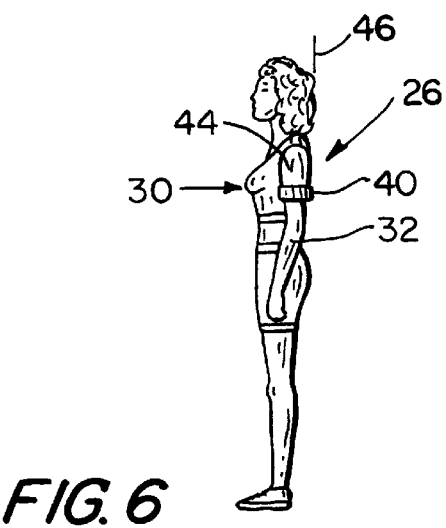
FIG. 5
FIG. 6

POSTURE-AIDING DEVICE

The present invention relates generally to an extended utilitarian use of an elastic closed-loop band, wherein it significantly enhances the posture of the user.

EXAMPLES OF THE PRIOR ART

Using to advantage stretch fabric, i.e. fabric with rubber or elastomeric yarn content, such fabric made up as closed loops or bands are already in wide use for exercising wherein, in a typical exercising routine, the user positions his/her arms through the loop and alternately widens and narrows the spacing between the arms, so that widening is against the resistance of the fabric and narrowing against the urgency thereof, and this exercising routine, typically called isometrics, significantly contributes to muscle development. Elastic bands used for isometrics, as just described, are exemplified by U.S. Pat. No. 2,224,103 for "Exercising Apparatus" issued to R. E. Nilson on Dec. 3, 1940, U.S. Pat. No. 3,819,177 for "Elastic Exercise Belt" issued to Irving Spiro on Jun. 25, 1974 and U.S. Pat. No. 5,230,682 for "Exercise Device" issued to Marguerite J. Meyers on Jul. 27, 1993, to mention but a few prior patents.

The referenced elastic bands and all other known similar articles of manufacture are used according to prior art practice for muscle development, and thus have a mode of use which can only be of a limited duration because the use produces attendant fatigue.

Broadly, it is an object of the present invention to provide an elastic band article of manufacture having a non-straining or fatiguing mode of use, and yet of significant beneficial value to the user, overcoming the foregoing and other shortcomings of the prior art.

More particularly, it is an object to use the urgency of the stretch construction material of the closed loop band as a posture-aiding device, it having been found to be effective in developing a habit in the user against slouching his/her shoulders and assuming shoulder positions in a vertical plane having a favorable contribution to the user's appearance, all as will be better understood as the description proceeds.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a perspective view of an elastic band demonstrating prior art use for isometric-type exercises;

FIG. 2 is a perspective view of an elastic band suitable for exercising use according to prior art practice, but prescribed herein as a posture-aiding device according to the present invention;

FIGS. 3–6 are perspective views demonstrating, in sequence, the manner in which the elastic band of FIG. 2 is used as a posture-aiding device wherein, more particularly, FIG. 1 is a front elevational view illustrating, in the fitting of the elastic band upon the user, the positioning of one arm of the user through the opening of the band;

FIG. 4 illustrates the positioning of the other arm of the user through the opening of the band;

FIG. 5 is a rear elevational view which illustrates the operative position of the band contributing to its posture-aiding function;

FIG. 6 is a side elevational view further illustrating the posture-aiding functioning of the band.

Figure 7:
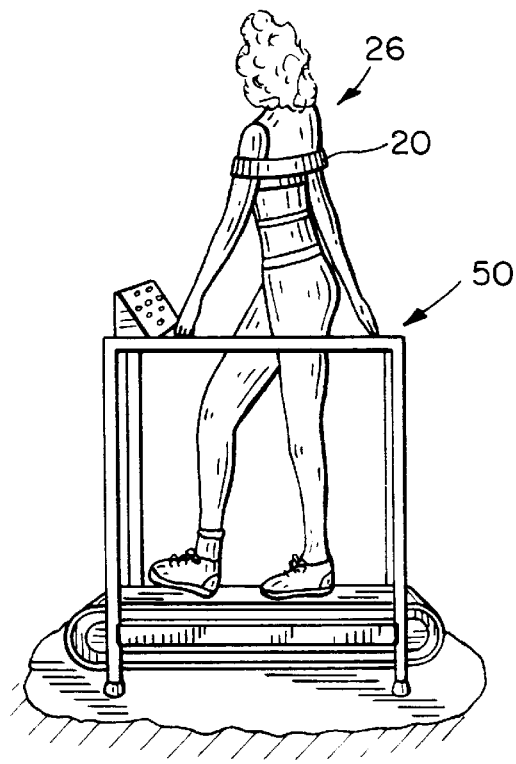
FIGS. 7, 8 and 9 are perspective views illustrating posture-aiding end uses of the within inventive band.
Figure 8:
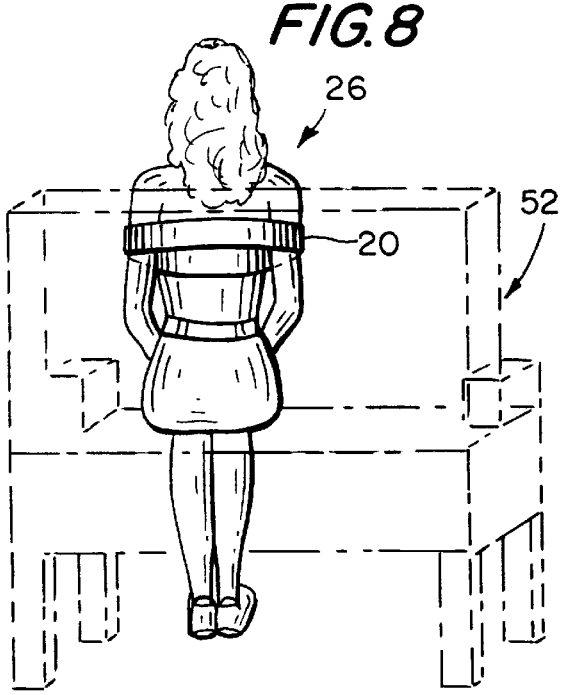
Figure 9:
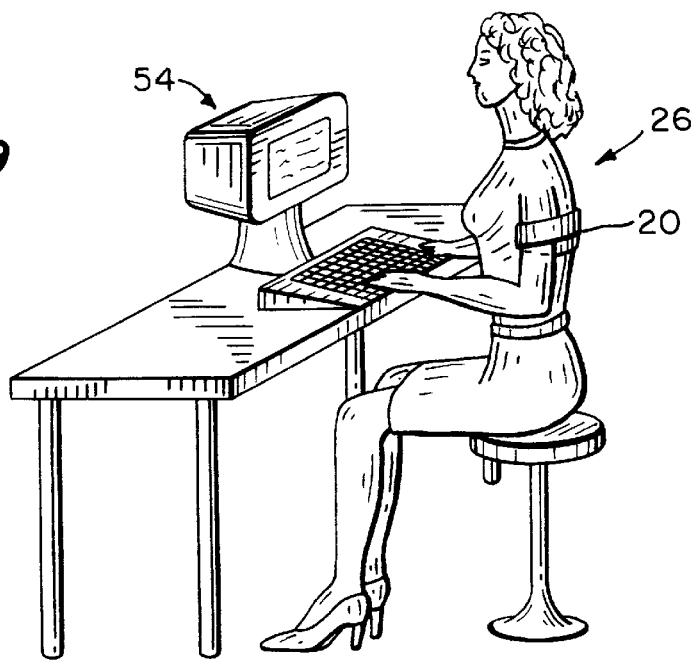

Using to advantage the stretch of fabric with rubber or elastomeric content, it is already known, as illustrated in FIG. 1, that such stretch fabric 10, which is readily commercially available, can appropriately be formed into a closed loop 12 and, as one typical exercise routine, be used by the exerciser projecting or positioning his/her arms 14 through the opening 16 of the loop 12 and alternately moving the positioned arms 14 apart against the resistance of the stretch fabric 10 and returning to the starting spaced-apart position of the arms 14, and doing so again against the resistance or more aptly the urgency of the stretch fabric 10, the above described exercising activity being typically called isometrics. The FIG. 1 prior use of the stretch band 12 primarily contributes only to muscle development and, as should be obvious, can only be of a limited duration because it produces attendant fatigue.

FIG. 2, to which reference should now be made, illustrates an article of manufacture specifically of stretch fabric material 18 construction formed into a closed loop band 20 having a manufactured side-to-side width 22 that is selected to be slightly undersized (FIG. 3) with respect to the back width 24 (FIG. 5) of a user. For a female, measurements in a study entitled "Anthropometry of Air Force Women" indicate that back widths, such as width 24, do not significantly vary, but that size variation in girth is due mainly to variations in bust size. Underlying the present invention is the recognition that by thusly limiting in the fitting of the stretch band 20 particularly to a female user 26 to an operative position, as illustrated in FIG. 5, in which it spans only across the back 28 of the user 26, and thus is not in encircling relation across the chest or bust 30 of the user, that the stretch band 20 as a one-size-fits-all article of manufacture can be effectively used as a posture-aiding device, when in the operative position as shown in FIGS. 5 and 6.

More particularly, and as will be better understood from the fitting steps illustrated in sequence in FIGS. 3–5, user 26 positions her left arm 32 through the stretch band 20 and, maintaining the thusly engaged band 20 rearwardly of her body, slips her right arm 34 through the opening 36 of the band 20, much like an individual putting on a coat and positioning arms through the coat sleeves.

The operative position that results is shown in FIG. 5, wherein the length portions of the band adjacent the arms 32 and 34 are functionally arm-receiving opposite end loop configurations, as at 38 and 40, and exert an urgency 42 from opposite directions inwardly of the user's back. The urgency 42 will be understood to be of a nominal extent by appropriate selection of the stretch characteristics of the stretch fabric 18, which nominal extent is far less than the urgency experienced using the exercising band of FIG. 1, and thus does not contribute to fatigue, but is of an extent effective to urge the upper arms or shoulders 44 of the user into a vertical plane 46 of the user's back, as best illustrated in FIG. 6. The posture illustrated in FIG. 6 is of a desirable nature because of its favorable contribution to the user's appearance, and in practice it has been found that the FIG. 5 operative position of the band 20 can be worn for relatively long durations without discomfort, as for example several hours while watching television, reading a book or like activity, and that this usage is effective to develop a habit in the user against slouching his/her shoulders and assuming a less desirable posture. Exemplary of the recommended end uses of the band 20 are illustrated in the posture-aiding position on the user 26 in relation to a treadmill 50, sitting on a couch 52 and working at a computer station 54, during which the band 20 functions as already described to inculcate a habit for a good posture without interfering with the activities noted.

Although the specifications of what would be an appropriate stretch band 20 to be used as a posture-aiding device according to the present invention should be readily understood by one well versed in the art, it is noted that good results have been obtained using stretch fabric commercially available from Sullivan-Carson, Inc. of York, S.C., specified as surgical webbing of 82% polyester, 6% nylon, and 12% latex rubber. The height of the band is three inches, plus or minus 1/8 of an inch, and is effective for fitting as one-size-fits-all in a side-to-side width of approximately 14 1/4 inches. Optionally, however, the width size of 14 1/4 inches can be used for a size range of "small to medium" and a size range specified for "medium to large" can use a side-to-side width of approximately 16 1/2 inches.

While the posture-aiding stretch band herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method improving posture comprising the steps of forming a closed loop of stretch material, horizontally positioning a length portion of said closed loop flat against a back of a user, forming opposite left and right arm loops extending laterally on opposite sides of said flat length portion of said closed loop, positioning said left and right arm loops respectively upon a left and right upper arm of a user, and stretching said closed loop in a horizontal direction during said positioning thereof upon said user's left and right upper arms, whereby said stretched closed loop manifests an urgency to return to said unstretched condition to obviate a slouching posture.

* * * * *